US00PP12553P2

(12) United States Plant Patent
Drewlow

(10) Patent No.: US PP12,553 P2
(45) Date of Patent: Apr. 16, 2002

(54) NEW GUINEA IMPATIENS PLANT NAMED 'OVATION RED'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/550,512

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Red, characterized by its deep, bright red flower color, large flower diameter, bright green leaves, continuous, and long-lasting flowering, self-branching and vigorous habit.

1 Drawing Sheet

The present invention relates to a new and distinctive cultivar of Impatiens plant, botanically known as *Impatiens Hawkeri*, commercially known as New Guinea Impatiens, and known by the cultivar name 'Ovation Red'. Ovation Red was developed in a controlled breeding program by crossing Prepona, U.S. Plant Pat. No. 9,150 (seed parent) with Mikkelsen Seedling No. 95-310-1 (pollen parent). The pollen parent is a proprietary breeding line which has not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguishes the new Impatiens from both its parent varieties and other cultivated Impatiens of this type known and used in the floriculture industry:

1. Ovation Red has deep, bright red flowers similar in color to Prepona (U.S. Plant Pat. No. 9,150) and a shade lighter than Celebration Deep Red (U.S. Plant Pat. No. 9,521).
2. Ovation Red has a larger flower diameter (7.0 to 7.5 cm) than either Prepona or Celebration Deep Red (6.5 to 7.0 cm).
3. Ovation Red has bright green leaves which are similar to those of Celebration Deep Red but much darker than the yellow-green leaves of Prepona.
4. Ovation Red and Celebration Deep Red have a similar leaf length (9 to 10 cm) and width (3.0 to 3.5), which is smaller in length and width than Prepona (11 to 12 cm long and 4 cm wide), on an average mature leaf.
5. Ovation Red has a more mounded growth habit than Prepona and Celebration Deep Red and is more compact than Celebration Deep Red and similar to Prepona.
6. The underside of the leaves of Ovation Red and Prepona have a red-purple color to the midrib and veins while Celebration Deep Red has green veins and midrib.
7. Ovation Red retains its growth habit and flowering under high temperature and light conditions while Prepona and Celebration Deep Red lose plant habit and flowering under the same conditions.
8. Ovation Red has a reddish-purple ovary color, while Prepona and Celebration Deep Red both have green colored ovaries.

9. Ovation Red has a heavy reddish cast to the stem which is similar to Prepona, but Celebration Deep Red has a green stem with a reddish cast in the area of the node.
10. The small flower buds of Ovation Red have a reddish cast while Prepona and Celebration Deep Red have a green bud color.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. Fertilizer regime: constant feed; 20 ppm $N_2$, 75 ppm K, 200 ppm P. The plants were grown at 16° C. night temperatures, under 3000 to 4000 foot candles of light and with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary significance are used.

Parentage: A controlled cross between female parent, Prepona, U.S. Plant Pat. No. 9,150 and male parent Mikkelsen Seedling No. 95-310-1.

Propagation:

(*A*) *Type cutting.*—Stem tip 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fibrous.

Plant description:

(*A*) *Form and habit of growth.*—Mounded, self-branching, intermediate in height, flowers open over the top of leaf canopy; continuous flowering; vigorous growing flowering herb. Average height is 18 to 22 cm and average width is 40 to 45 cm. Internode length is 5 to 6 cm but is highly variable. Pedicel is Greyed-Purple Group 185B, stem is Yellow-Green Group 148A with a Greyed-Purple Group 184C cast, and internode is Yellow-Green Group 148A with a Greyed-Purple Group 184C cast. Pedicel length is 5 cm.

(*B*) *Foliage description.*—Bright green with yellow-green and reddish cast near leaf base midrib; underside of leaf has reddish veins and midrib; no leaf variegation. (1) Size: 9 to 10 cm long and 3.0 to 3.5 cm wide on average mature leaf. (2) Shape: Lanceolate with acuminate apex and acute base. (3) Texture: Both upper and lower surfaces are glabrous. (4) Margin: Entire, with fine cilia. (5) Color: Young foliage, top side is Yellow-Green Group 146A, underside is Yellow-Green Group 137C. Mature foliage, top side is Green Group 137A, underside is Green Group 137C. (6) Venation: Pinnate, upper side is Yellow-Green Group 147B and lower side is Greyed-Purple Group 185B. (7) Young midrib is Yellow-Green Group 147C with a Greyed-Purple Group 185B cast and mature midrib is Yellow-Green Group 147D with a Greyed-Purple Group 185B cast.

(*C*) *Branching.*—The branching is naturally occurring. Lateral branching at base: 5 or more lateral branches. Lateral branch length is 12 to 15 cm but is highly variable.

Flowering description:

(*A*) *Flowering habits.*—Flowers continuously from leaf whorl in a progressively orderly manner with one flower per leaf axil. When the last flower in a whorl opens, the first flower in the leaf whorl above starts to open. It takes 5 to 7 days for a mature bud to fully open and the flower may last two weeks or longer depending on the environment. The time to first flower is approximately 8 weeks from root cuttings. The flowers are self-cleaning.

(*B*) *Natural flowering season.*—Indeterminate and continuous; quantity of flowering increases with increasing levels of light.

(*C*) *Flower bud.*—Ellipsoidal; flowers perfect; spur is 4.5 cm long on mature bud with the throat behind the ovary and originating from the major sepal. Bud length is 18 to 20 mm and bud diameter is 16 mm. Spur is Greyed-Purple Group 185B, spur tip is Greyed-Purple Group 185A, and flower bud is Red Group 45A just before opening.

(*D*) *Flowers borne.*—On individual Red-Purple Group 185B 5.0 to 5.5 cm long from a whorl of usually five leaves. Flowering progressively around the whorls as buds and leaves develop. Leaf axils have one flower each.

(*E*) *Quantity of flowers.*—Numerous because of self-branching nature of plant and the long-lasting flower characteristic.

(*F*) *Diameter of flower.*—7.0 to 7.5 cm. Flower Depth: 5 mm.

(*G*) *Petals.*—(1) Shape: Heart. (2) Color: Top side in winter when opening is Red Group 45C. (3) Number of petals: Five. (4) Size of petals: Standard: 4.5 cm wide and 3.0 cm long, two equal lobes with shallow cut. Wings: 3.5 cm wide and 3.0 cm long, two unequal lobes with shallow cut. Keel: 4.0 cm wide and 3.5 cm long, two unequal lobes with deep cut.

(*H*) *Reproductive organs.*—(1) Stamens: Five in number. (a) Anther: Hooded shape, color is Red Group 45B. (b) Pollen color: Yellow-White Group 158C. (2) Pistils: (a) Stigma: Five, segmented column, color is Red-Purple Group 62C. (b) Style color: Reddish-purple. (c) Ovaries: Five in number, size is 6 mm when immature, color is Yellow-Green Group 146B.

(*I*) *Fertility.*—The plants are fertile, but do not normally set seed under greenhouse or garden conditions, unless in a controlled crossing program. Disease resistance: No significant disease or insect problems seen to date.

OTHER IMPORTANT CHARACTERISTICS

1. Self-branching, early flowering nature allows cultivar to be grown in 10 cm pots but is also very vigorous enough to be grown in 15 to 25 cm containers as well.

2. Minimal fading of older flowers and large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Red, as illustrated and described.

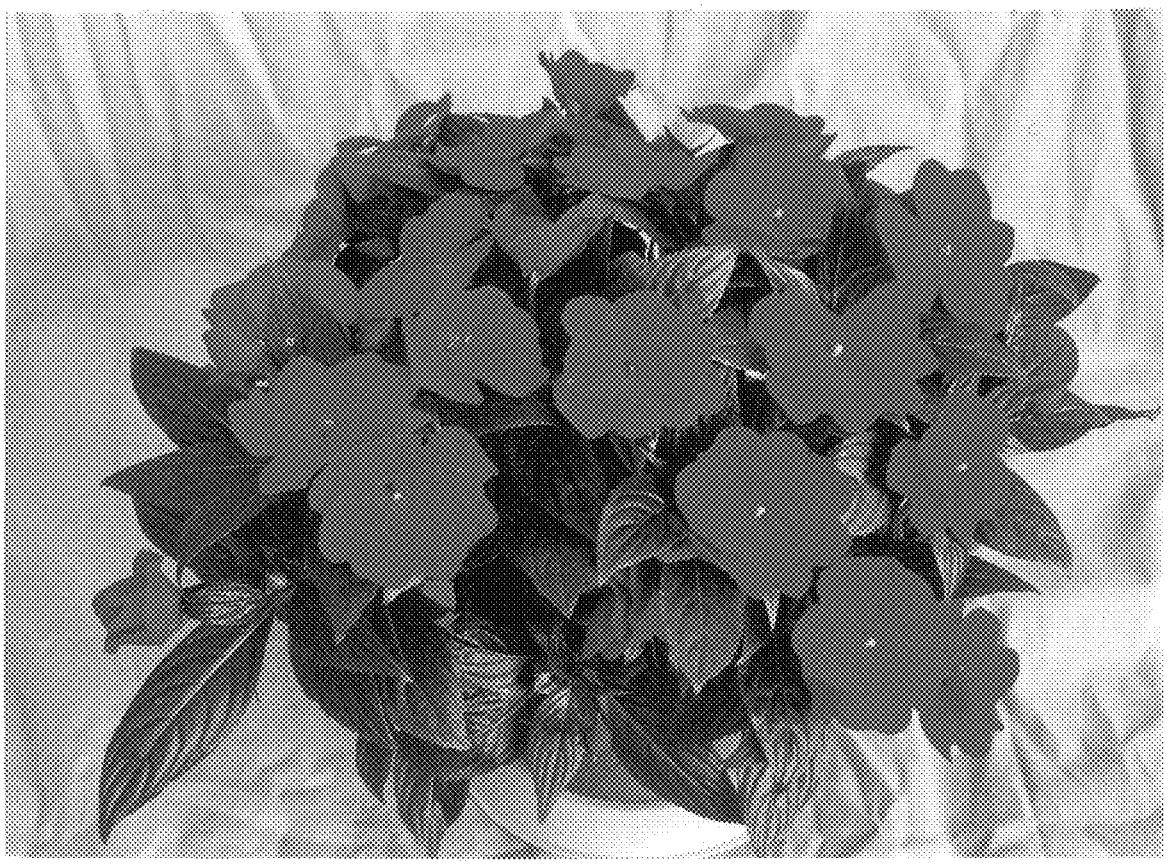

* * * * *